United States Patent [19]

Richmond

[11] Patent Number: 5,298,024
[45] Date of Patent: Mar. 29, 1994

[54] MULTI-LIQUID MEDICAMENT DELIVERY SYSTEM WITH REFLEX VALVES

[76] Inventor: Frank Richmond, 205 A Grant St., Harvard, Ill. 60033

[21] Appl. No.: 997,522

[22] Filed: Dec. 28, 1992

[51] Int. Cl.⁵ .......................................... A61M 37/00
[52] U.S. Cl. ........................................ 604/90; 604/88; 604/191
[58] Field of Search ............... 604/194–199, 604/218, 231–232, 235, 236, 237, 249, 82–93, 200–205, 225, 226, 244–246, 68, 70, 81, 183, 184, 139, 71, 131, 149, 191, 150

[56] References Cited

U.S. PATENT DOCUMENTS

| | | | |
|---|---|---|---|
| 3,911,916 | 10/1975 | Stevens | 604/191 |
| 4,643,721 | 2/1987 | Brunet | 604/191 |
| 4,683,916 | 8/1987 | Raines | 137/854 |
| 5,102,388 | 4/1992 | Richmond | 604/88 |
| 5,215,524 | 6/1993 | Vallenlunga et al. | 604/110 |

OTHER PUBLICATIONS

Vaclok Medallion Syringe Brochure–Merit Medical–-Salt Lake City, Utah 84107.

Primary Examiner—C. Fred Rosenbaum
Assistant Examiner—Alexander
Attorney, Agent, or Firm—John L. Rogitz

[57] ABSTRACT

A syringe for sequentially injecting a plurality of liquids into an intravenous (IV) infusion component that has a connector fitting includes a syringe vessel having a preferably needleless injection port that is engageable with the connector fitting of the IV component. A syringe plunger is slidably disposed in the syringe vessel, and at least one barrier plunger is slidably disposed in the syringe vessel between the injection port and the syringe plunger. The barrier plunger is formed with a pathway for fluid communication therethrough, and a valve is positioned in the pathway of the barrier plunger to block fluid communication through the pathway. A nipple extends inwardly from the injection port for opening the valve of the barrier plunger when the barrier plunger is urged against the nipple. A first liquid is disposed in the syringe vessel between the barrier plunger and the injection port and a second liquid is disposed in the syringe vessel between the two plungers. The syringe plunger can be advanced against the second liquid toward the injection port, thereby urging the barrier plunger against the first liquid to expel the first liquid through the injection port. As the syringe plunger is advanced further into the vessel, the barrier plunger is urged against the nipple of the injection port to open the valve, thereby establishing a pathway for fluid communication through the channel of the barrier plunger for expelling the second liquid through the injection port.

20 Claims, 2 Drawing Sheets

MULTI-LIQUID MEDICAMENT DELIVERY SYSTEM WITH REFLEX VALVES

FIELD OF THE INVENTION

The present invention relates generally to systems that deliver liquid medicaments intravenously, and more particularly to systems that deliver a plurality of liquid medicaments intravenously.

BACKGROUND

Many modern medical therapies require the intravenous (IV) infusion of liquid medicaments into the patient undergoing treatment. Typical liquid medicaments include simple saline solutions, to prevent patient dehydration, solutions containing nutrients for the patient, and solutions that contain medicinal compounds. These liquid medicaments can be infused into the patient by, e.g., gravity drain from an elevated IV bag into the patient, pumping the liquid medicament from a medicament source into the patient, or any other method which is appropriate for the particular therapy and patient.

Ordinarily, the liquid is infused into the patient by connecting the liquid source to one end of an IV line, attaching a needle to the other end of the line, and inserting the needle into the patient. Regardless of how the particular IV infusion therapy is effected, however, the need occasionally arises to infuse other medicaments, in addition to the medicament being infused, into the patient. Commonly, this means that a second needle must be inserted into the patient or injection site. It can be appreciated that this is uncomfortable for the patient and may introduce additional hazard to the health care worker. Moreover, the use of needles preferably should be minimized, to minimize the chances of health care workers inadvertently puncturing themselves with needles, which can be especially nettlesome in the era of AIDS.

Accordingly, devices have been developed which permit the infusion of more than one medicament type through a single IV line. For example, connectors familiarly referred to as injection sites (i.e., "Y"-site or "T"-site valves because of their shape) have been introduced. A Y-site valve has a first port that can be connected to an IV line leading to the source of the liquid medicament to be infused, a second port that can be connected to an IV line leading to the patient, and a third port that can be connected to a second source of liquid medicament. Flow from the first source can be stopped, e.g., by engaging a roller clamp with the IV line leading to the source and then operating the roller clamp to collapse the line, and the infusion of liquid from the second source into the patient can be then be effected through the Y-site valve and the IV line that leads to the patient. Alternatively, a check valve can be positioned just up stream of the Y-site valve or T-site valve.

It is sometimes the case, however, that infusion of a first type of medicament through an IV line into a patient or another IV component, such as an IV bag, cannot immediately precede the infusion of a second type of medicament through the same IV line. This is because some medicaments are not compatible with certain other medicaments. Accordingly, when it is desired to infuse a second medicament into, for example, a patient, through an IV line through which a first medicament which is incompatible with the second medicament has been infused, infusion of the first medicament through the IV line must be halted. Then, a source of flushing fluid must be connected to the Y-site valve, and fluid infused through the Y-site valve and IV line to flush the line.

Next, the source of flushing fluid must be disconnected from the Y-site valve, and the source of the second medicament connected to the valve. Then, the second medicament is infused into the patient. After infusion of the second medicament, the source of the second medicament must be disconnected from the Y-site valve, the IV line flushed again, and the source of the first medicament reconnected to resume the IV therapy.

Understandably, the disconnecting and connecting of a series of IV lines to a single injection site valve can be a time-consuming, labor-intensive evolution, and can also lead to human error in connecting and disconnecting the lines in proper sequence and potential leaking of the injection site. Such mistakes can not only result in ineffective IV infusion therapy, but can also cause grave complications in the patient.

Accordingly, it is an object of the present invention to provide a syringe for infusing a plurality of medicaments into a patient in a predetermined sequence. It is another object of the present invention to provide a syringe which reduces the need to use needles or other sharp components. A further object of the present invention is to provide a syringe for infusing a plurality of liquid medicaments into a patient in a predetermined order, without requiring repeated connections and disconnections of IV lines to an IV connector. Another object of the present invention is to provide a syringe for infusing a plurality of liquid medicaments into a patient in a predetermined order which is easy to use and cost-effective to manufacture.

SUMMARY OF THE INVENTION

A delivery system for sequentially infusing a plurality of liquid medicaments into a patient, or multiple doses of the same medicament into the patient, includes a needleless syringe vessel having a wall and an injection port formed through the wall. Preferably, the injection port is configured for engaging a needleless connector fitting of an intravenous (IV) component. The IV component can be any appropriate device, such as an IV line, an IV infusion bag, an IV infusion bottle, or an IV valved connector. Thus, in one preferred embodiment, the injection port includes a luer fitting for engaging a complementary connector fitting on an IV infusion component, and can thus infuse fluid into the IV infusion component without resorting to the use of needles.

As envisioned by the present invention, a syringe plunger is slidably disposed in the syringe vessel, and at least one barrier plunger is also slidably disposed in the syringe vessel between the syringe plunger and the injection port. A first liquid medicament is disposed in the syringe vessel between the barrier plunger and the injection port, and a second liquid medicament is disposed within the syringe vessel between the two plungers. Preferably, to facilitate advancing the syringe plunger into the syringe vessel, a handle is attached to the syringe plunger. The handle can include one or more resilient stops which engage the wall of the syringe vessel as the syringe plunger is advanced into the vessel, to provide a tactile indication to the operator of the position of the syringe plunger relative to the vessel.

In accordance with the present invention, the barrier plunger is formed with a channel, and the channel extends through the barrier plunger. Preferably, the channel is formed coaxially with the barrier plunger. The barrier plunger also has a means for selectively blocking the channel. This blocking means is biased to a closed configuration, wherein no fluid communication is permitted to flow through the channel. Additionally, the blocking means has an open configuration, wherein a pathway for fluid communication is established through the channel, i.e., wherein a pathway is established which permits the second liquid medicament to flow through the barrier plunger to the injection port.

In accordance with the presently preferred embodiment of the present invention, the blocking means is a valve that includes a hollow body defining a fluid passageway, and a valve seat circumscribes the fluid passageway. Additionally, the valve includes a resilient valve disc that is positioned in the fluid passageway. The disc is biased into a closed position, wherein the disc abuts the valve seat and thereby blocks fluid flow through the fluid passageway. The disc is movable to an open position, wherein the disc is distanced from the valve seat so that fluid flow is permitted through the fluid passageway.

As contemplated by the present invention, the valve body has a support element which is positioned on the valve body between the valve disc and the inside of the IV bag for supporting the valve disc at the center of the disc. Also, the valve body includes a retainer element that is positioned on the opposite side of the disc from the support element, to hold the center of the disc against the support element. Also, the valve has an urging member that is reciprocally disposed in the fluid passageway of the valve on the same side of the disc as the retainer element. This urging member is movable between a first position, wherein the urging member is distanced from the valve disc, and a second position, wherein the urging member contacts the valve disc to move the disc into its open position.

The injection port includes a nipple protruding inwardly toward the barrier plunger. When the syringe plunger is urged into the syringe vessel, i.e., against the second liquid medicament, fluid pressure is generated by the second liquid medicament against the barrier plunger. This in turn causes the barrier plunger to slide within the syringe vessel toward the injection port and thus to urge against the first liquid medicament, which causes the first liquid medicament to be expelled through the injection port and out of the syringe vessel.

As the syringe plunger is advanced further towards the injection port, the barrier plunger eventually abuts against the nipple of the injection port, which is configured for engaging the valve when the barrier plunger is urged against it and thereby move the valve to its second, i.e., open, position. In other words, when the barrier plunger is urged against the nipple of the injection port, the nipple of the injection port urges against the urging member. This establishes the open configuration of the valve and thereby permits the second liquid medicament to flow through the channel of the barrier plunger and out of the injection port as the syringe plunger is advanced further toward the injection port.

In accordance with the above disclosure, the first liquid medicament can be a saline solution for flushing the residue of earlier-infused medicaments out of the IV connector fitting into which the first liquid medicament is infused. On the other hand, the second liquid medicament can be a medicament which may not be compatible with the earlier-infused medicaments but which may nevertheless be safely infused into a patient through the IV connector fitting because of the flushing effect of the first liquid medicament.

If desired, yet a third liquid medicament can be held within the syringe vessel and expelled from the vessel through the injection port after the first and then the second liquid medicaments have been expelled. When a third liquid medicament is to be used, a third plunger is slidably disposed in the syringe vessel between the second liquid medicament and the syringe plunger, and the third liquid is disposed in the syringe vessel between the syringe plunger and the third plunger. Additional compartments can be added in accordance with the principles of the present invention.

Like the barrier plunger, the third plunger has a channel formed therethrough and a valve disposed in the channel for selectively blocking fluid communication through the channel. A nipple is formed on the barrier plunger to engage and thereby open the valve of the third plunger when the third plunger is urged against the barrier plunger. More particularly, when the second medicament has been ejected from the syringe, the barrier plunger rests against the nipple of the injection port. As the syringe plunger is advanced further into the syringe, the third plunger is forced against the nipple of the barrier plunger, and the valve of the third plunger is thereby opened. Consequently, a path for fluid communication is established for the third fluid to be expelled from the syringe injection port through the open valves of the third plunger and the barrier plunger.

The details of the construction of the present invention, as well as the operation of the present invention, can best be understood in reference to the accompanying drawings, in which like numerals refer to like parts, and in which:

DESCRIPTION OF THE PREFERRED EMBODIMENT

Figure 1:
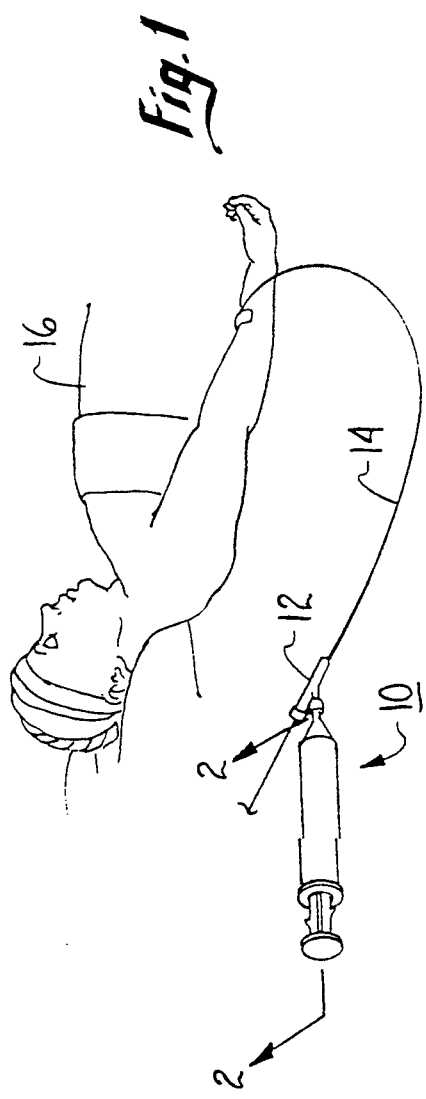
FIG. 1 is a perspective view of the liquid medicament delivery system of the present invention, shown in one intended environment.

Referring initially to FIG. 1, a liquid medicament delivery system is shown, generally designated 10. As shown, the delivery system 10 can be engaged with a suitable intravenous (IV) infusion connector, such as the Y-site valve 12, for infusing liquid from the delivery system 10 through an IV line 14 into a patient 16. Preferably, the Y-site valve is a needleless connector, i.e., the ports of the Y-site valve are configured for engaging another complementary needleless connector, such as a luer fitting.

Figure 2:
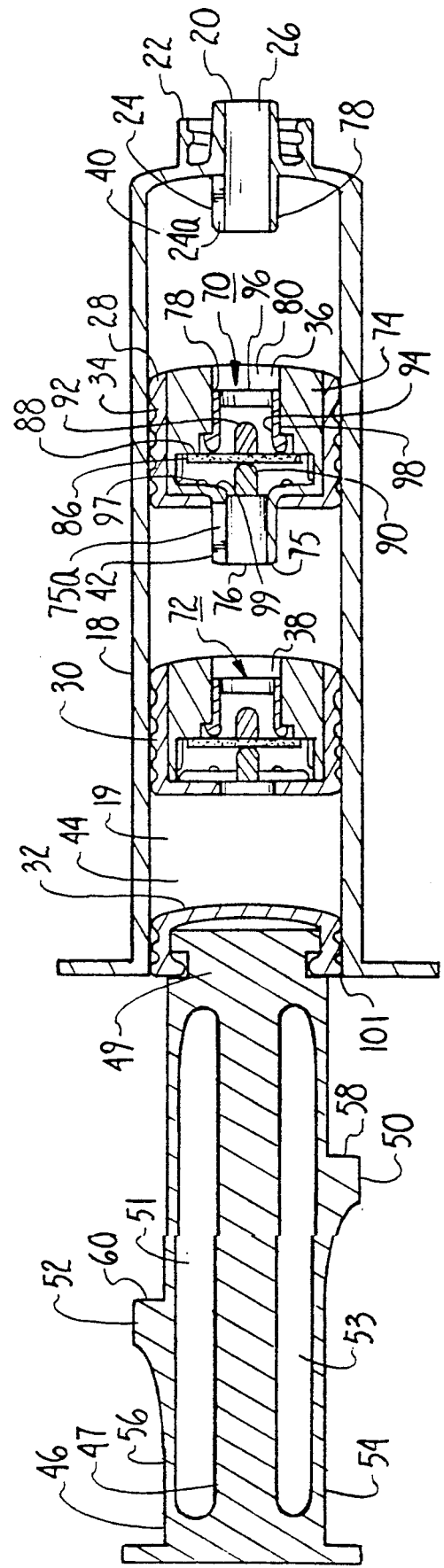
FIG. 2 is a cross-sectional view of the liquid medicament delivery system of the present invention, as seen along the line 2—2 in FIG. 1.

Referring now to FIG. 2, the details of the system 10 can be seen. As shown in FIG. 2, the system 10 is essentially a syringe having a plurality of fluid medicaments therein. More specifically, the system 10 includes an elongated, generally cylindrical syringe vessel 18 forming a chamber 19, and the vessel 18 has a port 20 formed in one end thereof. Preferably, the port 20 includes a luer fitting 22 for engaging a complementary luer fitting (e.g., one of the luer fitting on the Y-site valve 12). The luer fitting 22 can be a male luer fitting, as shown, or a female luer fitting, as appropriate for the particular application of the system 10.

Additionally, FIG. 2 shows that the port 20 has an inwardly-protruding nipple 24. A passageway 26 is established by the port 20 for permitting fluid communication out of the chamber 19 through the passageway 26. The syringe vessel 18 and associated port 20 are made of a biocompatible material, such as transparent glass or plastic, that is suitable for use as a syringe.

FIG. 2 shows that the system 10 has a plurality of plungers for sequentially urging a plurality of fluids out of the chamber 19. In the embodiment shown, three plungers are serially disposed in the chamber 19. More particularly, first and second barrier plungers 28, 30 are slidably disposed in the chamber 19, and a syringe plunger 32 is slidably disposed in the chamber 19. Each plunger 28, 30, 32 is made of a biocompatible resilient material, such as rubber, silicon, or urethane.

As can be appreciated in reference to FIG. 2, each plunger 28, 30, 32 is generally formed as a disc. Each plunger 28, 30, 32 has a plurality of ring-like lands that engage the inside wall of the syringe vessel 18 in an interference fit to form a fluid-tight seal between the particular plunger 28, 30, 32 and the syringe vessel 18. For example, the first barrier plunger 28 has lands 34 that engage the inside wall of the syringe vessel 18 in an interference fit to form a fluid-tight seal between the first barrier plunger 28 and the syringe vessel 18.

FIG. 2 further shows that each of the barrier plungers 28, 30 has a respective channel 36, 38 formed therethrough that establishes a pathway for fluid communication therethrough. Each channel 36, 38 is preferably coaxial with its respective plunger 28, 30. Moreover, means are provided in each plunger 28, 30 for blocking the associated channel 36, 38, as described more fully below.

In accordance with the disclosure above, it can be appreciated that a plurality of fluid medicaments can be held in the chamber 19 of the syringe vessel 18 separate from each other. Specifically, a first fluid 40 is held in the chamber 19 between the first barrier plunger 28 and the port 20. Also, a second fluid 42 is held in the chamber 19 between the first barrier plunger 28 and the second barrier plunger 30. Further, a third fluid 44 is held between the second barrier plunger 30 and the syringe plunger 32. These fluids 40, 42, 44 cannot mix with each other because of the fluid-tight seals between the fluids 40, 42, 44 which are established by the plungers 28, 30, 32. Consequently, the fluids 40, 42, 44 do not have to be compatible with each other. It is to be understood that each of the fluids 40, 42, 44 can be any appropriate fluid, e.g., saline solution, haprin, medicinal compound, etc., for IV infusion to the patient 16.

Still referring to FIG. 2, a handle 46 is connected to the syringe plunger 32 for providing a means for advancing the syringe plunger 32 into the chamber 19 of the syringe vessel 18. Preferably, the handle 46 has an elongated shank 47 that is made of rigid plastic. To connect the handle 46 to the syringe plunger 32, the distal end 49 of the handle 46 is formed with a head 48, and the head 48 is embedded in the syringe. If desired, the head 48 of the handle 46 can be bonded to the syringe plunger 32. While FIG. 2 indicates that the head 48 is formed separately from the handle 46, it is to be understood that for ease of manufacture, the head 48 can be formed integrally with the handle 46.

In the presently preferred embodiment, the handle 46 includes a means for providing a tactile indication to the operation of the system 10 of the position of the handle 46 relative to the syringe vessel 18. More particularly, the handle 46 is preferably formed with first and second elongated resilient stops 50, 52. Each stop 50, 52 is connected to the handle 46 at the respective proximal end 54, 56 of the particular stop 50, 52, and a space 51, 53 is formed in the handle 46 between the respective stops 50, 52 and the shank 47 of the handle 46. Also, each stop 50, 52 has a respective distal face 58, 60, and each face 58, 60 has a surface that is substantially perpendicular to the axis of the handle 46. Each stop 50, 52 is flexible, i.e., each stop 50, 52 can be depressed inwardly by an operator (not shown) toward the shank 47 of the handle 46.

As mentioned above and shown in FIG. 2, the first and second barrier plungers 28, 30 include means for selectively blocking their respective channels 36, 38. Specifically, as shown in FIG. 2, each channel 36, 38 has a respective valve, generally designated 70, 72 positioned therein for selectively blocking the channel 36, 38. The valves 70, 72 are substantially identical in construction and operation.

Taking the valve 70 as an example of the blocking means of the present invention, the valve 70 includes a rigid, preferably plastic (e.g., urethane) valve body 74 that has a fluid inlet 76, a fluid outlet 78, and a fluid passageway 80 formed in the valve body 74 between the inlet 76 and outlet 78. The valve body 74 can be a unitary structure, or be made of two or more pieces that are bonded together. For example, the inlet 76 can be made from a first piece, the outlet 78 can be made from a second piece, and the two pieces bonded together by means well-known in the art, e.g., solvent bonding, ultrasonic welding, or rf sealing.

The valve 70 also includes a flexible resilient plastic disc 86 that is disposed in the fluid passageway 80. Specifically, the periphery of the plastic disc 86 rests on a seating surface 88 of the valve body 74 to establish a fluid-tight seal between the disc 86 and seating surface 88. In other words, the valve disc 86 is biased to the closed configuration shown in FIG. 2.

Also, a support element 90 is formed in the fluid passageway 80 and extends across the fluid passageway 80. The support element 90 supports the disc 86 in the center thereof. To this end, a slight depression may be formed in the center of the disc 86 to receive the support element 90 and thereby prevent side-to-side motion of the disc 86 relative to the support element 90. As shown, the support element 90 is shaped as a cylinder, but it is to be understood that the support element 90 can have other suitable shapes, e.g., the support element 90 can have a triangular shape.

Additionally, a retainer element 92 is formed on the valve body 74 and extends across the fluid passageway 80. As shown, the retainer element 92 is positioned on the valve body 74 on the opposite side of the valve disc 86 from the support element 90. Accordingly, the retainer element 92 holds the center of the valve disc 86 against the support element 90.

Still referring to FIG. 2, a rigid urging member 94 is shown slidably disposed in the fluid passageway 80 for reciprocal movement therein. As shown, the urging member 94 has an annular head 96 and a skirt 98 that depends from the head 96. As further shown, the skirt 98 includes a plurality of, and preferably two, legs. The urging member 94 can be forced against the valve disc 86 when the nipple 24 is caused to abut against the urging member 94.

As can be appreciated in reference to FIG. 2, when the urging member 94 is forced against the valve disc 86, the skirt 98 of the urging member 94 contacts the disc 86. This deforms the valve disc 86, causing the periphery of the disc 86 to be distanced from the seating surface 88 of the valve body 74, and thereby permitting fluid communication through the fluid passageway 80. Stated differently, the urging member 94 can be forced against the valve disc 86 to deform the disc 86 into an open configuration. The resiliency of the valve disc 86 causes the disc 86 to resume its normally closed configuration, shown in FIG. 2, when the urging member 94 is not forced against the disc 86. Protrusions 97 can be formed on a surface 99 of the valve body 74 to prevent the establishment of a water seal between the disc 86 and the surface 99 when the disc 86 is deformed.

As also shown, a nipple 75 is attached to the first barrier plunger 28 and extends toward the channel 38 of the second barrier plunger 30. The nipple 75 can slide within the channel 38 of the second barrier plunger 30 and is configured for engaging the valve 70 of the second barrier plunger 30 when the second barrier plunger 30 is urged against the nipple 75.

As shown, the nipple 75 is generally cylindrical in shape, although other suitable configurations can be used. The nipple 75 is hollow, so that fluid can flow through the nipple 75 to the channel 36 of the first barrier plunger 28. FIG. 2 also shows that respective longitudinal grooves 75a, 24a are formed in the nipples 75, 24 for preventing a liquid seal from being established between the walls of the channels 38, 26 and the nipples 75, 24, respectively.

In the operation of the system 10, the luer fitting 22 of the system 10 is engaged with a component, e.g., the Y-site valve 12, through which it is desired to infuse fluid from the system 10. Next, an operator (not shown) advances the syringe plunger 32 into the syringe vessel 18 by appropriately manipulating the handle 46. As the syringe plunger 32 is advanced into the syringe vessel 18, the third fluid 44 is in turn caused to urge against the second barrier plunger 30. The second barrier plunger 30 is thereby caused to urge against the second fluid 42, which causes the second fluid 42 to urge against the first barrier plunger 28. The first barrier plunger 28 in turn is caused to advance into the first fluid 40, causing the first fluid 40 to be expelled through the fluid passageway 26.

Stated differently, when the system 10 is configured as shown in FIG. 2, a hydraulic lock exists within the syringe vessel 18. When the operator urges against the handle 46 to advance the syringe plunger 34 into the syringe vessel 18, the hydraulic lock transfers this force through the second and third fluids 42, 44 and the barrier plungers 28, 30 to cause the first fluid 40 to be expelled from the system 10 through the passageway 26.

Figure 3:
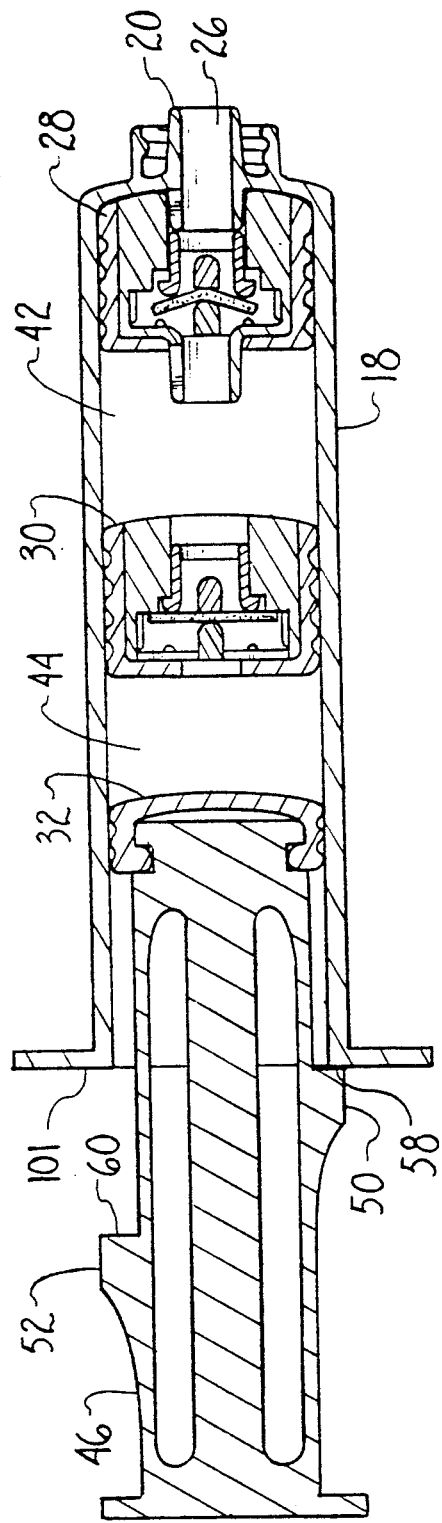
FIG. 3 is a cross-sectional view of the liquid medicament delivery system of the present invention, as would be seen along the line 2—2 in FIG. 1, with the handle partially advanced into the syringe further than as shown in FIG. 2.

When the first barrier plunger 28 has been advanced sufficiently toward the port 20, the nipple 24 engages the channel 36 of the first barrier plunger 28 and urges against the urging member 94, which in turn causes the disc 86 to be distanced from the valve seat 88, as shown in FIG. 3. Residual first fluid 40 is not trapped between the first barrier plunger 28 and the syringe vessel 18, but instead flows proximally through the groove 24a of the nipple 24 of the port 20 and thence out of the port 20.

At this point, as shown in FIG. 3, the distal face 58 of the stop 50 abuts against the syringe vessel 18, preventing further advancement of the syringe plunger 34 into the syringe vessel 18. This provides a tactile indication to the operator that substantially all of the first fluid 40 has been expelled from the system 10. Also, it will be appreciated that once the nipple 24 has opened the valve 70 of the first barrier plunger 28, a passageway is established for the second fluid 42 to flow through the channel 36 of the first barrier plunger 28 and out of the port 20.

Accordingly, to expel the second fluid 42 from the syringe vessel 18, the operator depresses the stop 50 to permit the distal face 58 of the stop 50 to clear the periphery 101 of the syringe vessel 18, and then advances the syringe plunger 32 further into the syringe vessel 18. In other words, the operator pushes the stop 50 inwardly and urges against the handle 46 to advance the syringe plunger 32 into the syringe vessel 18, to expel the second fluid 42 through the channel 36 of the first barrier plunger 28 and port 20.

Figure 4:
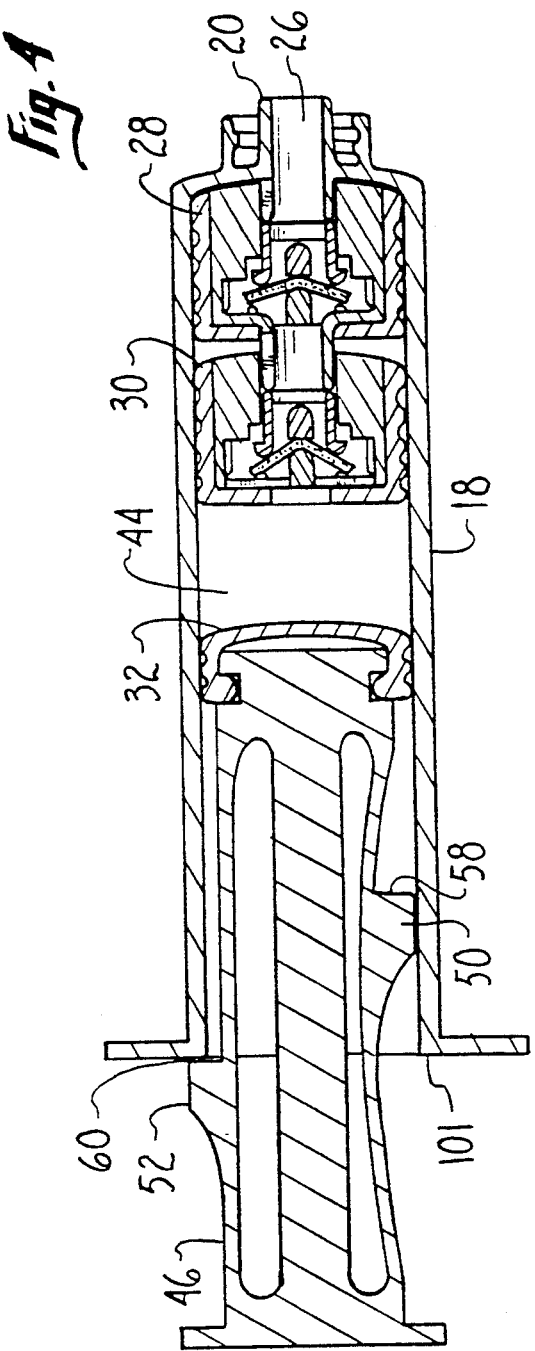
FIG. 4 is another cross-sectional view of the liquid medicament delivery system of the present invention, as would be seen along the line 2—2 in FIG. 1, with the handle advanced into the syringe further than as shown in FIG. 3.

When the syringe plunger 32 is advanced sufficiently into the syringe vessel 18, the channel 38 of the second barrier plunger 30 engages the nipple 75 of the first barrier plunger 28, thereby opening the valve 72 of the second barrier plunger 30, as shown in FIG. 4. Residual second fluid 42 is not trapped between the barrier plungers 28, 30, but flows through the groove 75a of the nipple 75 of the first barrier plunger 28 and into and through the channel 36 of the first barrier plunger 28.

At this point, as shown in FIG. 4, the distal face 60 of the stop 52 abuts against the syringe vessel 18, preventing further advancement of the syringe plunger 34 into the syringe vessel 18. Also, it will be appreciated that once the nipple 75 has opened the valve 72 of the second barrier plunger 30, a passageway is established for the third fluid 44 to flow through the channels 36, 38 of the barrier plungers 28, 30 and out of the port 20.

To expel third fluid 44 from the system 10, the operator depresses the stop 52 an amount sufficient to permit the distal face 60 of the stop 52 to clear the periphery 101 of the syringe vessel 18, and then urges against the handle 46 to advance the syringe plunger 32 into the third fluid 44. This causes the third fluid 44 to be expelled through the channels 36, 38 of the barrier plungers 28, 30 and through to port 20.

In accordance with the above disclosure, it can be appreciated that the present invention provides for the sequential infusion of two or more fluids that are held in a single syringe into an IV connector and thence into an IV line or other IV component. Also, the present invention provides a tactile indication to the operator of when each fluid held in the syringe has been expelled from the syringe, and prevents infusion of more than one of the fluids absent a positive act by the operator (i.e., depressing one of the stops 50, 52 as appropriate). Thus, multiple doses of a single medicament can be held in the syringe and infused without undue danger of over-infusion of more than a single dose at one time.

While the particular multi-liquid medicament delivery system as herein shown and described in detail is fully capable of achieving the above-stated objects, it is to be understood that it is but one embodiment of the present invention, that other embodiments are fully contemplated by the present invention, and that the scope of the present invention is accordingly to be limited by nothing other than the appended claims.

I claim:

1. A multi-liquid medicament delivery system, comprising:
    a syringe vessel having a wall and an injection port formed through the wall, the injection port being configured for engaging a needleless IV fitting;
    a syringe plunger slidably disposed in the syringe vessel;
    a barrier plunger slidably disposed in the syringe vessel between the syringe plunger and the injection port, the barrier plunger including a channel; and
    valve means for blocking the channel of the barrier plunger, the valve means having an open configuration, wherein fluid communication through the channel is permitted, and a closed configuration, wherein no fluid communication through the channel is permitted.

2. The system as recited in claim 1, further comprising a first liquid disposed in the syringe vessel between the barrier plunger and the injection port, and a second liquid disposed in the syringe vessel between the syringe plunger and the barrier plunger, for sequential expulsion of the liquids from the syringe vessel.

3. The system as recited in claim 2, wherein the injection port includes a nipple protruding inwardly toward the barrier plunger.

4. The system as recited in claim 3, wherein the valve means is biased to the closed configuration, and the nipple of the injection port is configured for engaging the valve means and moving the valve means to the open configuration.

5. The system as recited in claim 4, wherein the valve means is a valve, and the valve includes a hollow body defining a fluid passageway therethrough, the valve also including a resilient valve disc positioned in the fluid passageway and being biased into a closed configuration, wherein the disc blocks fluid flow through the fluid passageway, the disc being movable to an open configuration wherein fluid flow is permitted through the fluid passageway.

6. The system of claim 5, wherein the valve disc has a center and the valve further includes a support element positioned on the valve for supporting the valve disc at the center of the disc.

7. The system of claim 6, wherein the valve further includes a retainer element positioned in the valve on the opposite side of the disc from the support element, to hold the center of the disc against the support element.

8. The system of claim 7, further comprising an urging member reciprocally disposed in the fluid passageway of the valve on the same side of the disc as the retainer element, the urging member being movable between a first position, wherein the urging member is distanced from the valve disc, and a second position, wherein the urging member contacts the valve disc to move the disc into its open configuration.

9. The system of claim 8, wherein the urging member is moved to its second position by the nipple of the injection port.

10. The system as recited in claim 5, further comprising a handle attached to the syringe plunger.

11. The system as recited in claim 10, wherein the handle can be manipulated to urge the syringe plunger into the second liquid toward the injection port, thereby urging the barrier plunger into the first liquid to expel the first liquid through the injection port.

12. The system as recited in claim 11, wherein the handle can be manipulated to expel substantially all of the first liquid from the injection port and urge the barrier plunger against the nipple of the injection port to open the valve means, thereby establishing a pathway for fluid communication through the channel of the barrier plunger for expelling the second liquid through the injection port, the handle includes at least one stop for abutting the syringe vessel.

13. The system as recited in claim 12, further comprising a third plunger slidably disposed in the syringe vessel between the second liquid and the syringe plunger, and a third liquid disposed in the syringe vessel between the first and third plungers, the third plunger having a channel therethrough and means disposed in the channel for selectively blocking fluid communication through the channel.

14. A syringe for sequentially injecting a plurality of liquids into an intravenous (IV) infusion component having a needleless connector fitting, comprising:
    a syringe vessel having an injection port engageable with the connector fitting of the IV component;
    a syringe plunger slidably disposed in the syringe vessel;
    a barrier plunger slidably disposed in the syringe vessel between the injection port and the syringe plunger, the barrier plunger being formed with a pathway for fluid communication through the barrier plunger;
    a valve positioned in the pathway of the barrier plunger to block fluid communication therethrough; and
    a nipple extending inwardly from the injection port for opening the valve of the barrier plunger when the barrier plunger is urged against the nipple.

15. The syringe of claim 14, further comprising a first liquid disposed in the syringe vessel between the barrier plunger and the injection port and a second liquid disposed in the syringe vessel between the two plungers.

16. The syringe of claim 15, further comprising a third plunger slidably disposed in the syringe vessel between the second liquid and the syringe plunger, and a third liquid disposed in the syringe vessel between the syringe plunger and the third plunger, the third plunger having a channel formed therethrough and a valve disposed in the channel for selectively blocking fluid communication through the channel of the third plunger.

17. The syringe of claim 16, further comprising a handle attached to the syringe plunger, wherein the handle can be manipulated to urge the syringe plunger against the second liquid toward the injection port, thereby urging the barrier plunger against the first liquid to expel the first liquid through the injection port.

18. The syringe as recited in claim 17, wherein the handle can be manipulated to expel substantially all of the first liquid from the injection port and urge the barrier plunger against the nipple of the injection port to open the valve and thereby establish a pathway for fluid communication through the channel of the barrier plunger for expelling the second liquid through the injection port.

19. A system for holding a plurality of liquids and sequentially expelling the liquids from the system into a needleless connector fitting, comprising:
  a syringe vessel having an injection port engageable with the connector fitting, the vessel holding a first liquid and a second liquid;
  a barrier plunger slidably disposed in the syringe vessel between the two liquids, the barrier plunger being formed with a pathway for fluid communication through the barrier plunger;
  a valve positioned in the pathway of the barrier plunger to block fluid communication therethrough; and
  a nipple extending inwardly from the injection port for opening the valve of the barrier plunger when the barrier plunger is urged against the nipple.

20. The system of claim 19, further comprising a syringe plunger slidably disposed in the syringe vessel with the second liquid being disposed between the syringe plunger and the barrier plunger, the syringe plunger having a handle attached thereto for grasping the handle and urging the syringe plunger toward the injection port of the syringe vessel, thereby urging the barrier plunger toward the first liquid to expel the first liquid through the injection port.

* * * * *